US011151440B2

(12) United States Patent
Rodriguez Bravo et al.

(10) Patent No.: US 11,151,440 B2
(45) Date of Patent: Oct. 19, 2021

(54) NEURAL RESPONSE HUMAN DETECTOR

(71) Applicant: INTERNATIONAL BUSINESS MACHINES CORPORATION, Armonk, NY (US)

(72) Inventors: Cesar Augusto Rodriguez Bravo, Alajuela (CR); Erik Rueger, Ockenheim (DE)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 1016 days.

(21) Appl. No.: 15/806,904

(22) Filed: Nov. 8, 2017

(65) Prior Publication Data
US 2019/0138885 A1 May 9, 2019

(51) Int. Cl.
*G06N 3/04* (2006.01)
*G06N 3/08* (2006.01)
(Continued)

(52) U.S. Cl.
CPC .......... *G06N 3/0427* (2013.01); *A61B 5/378* (2021.01); *A61B 5/38* (2021.01); *A61B 5/7267* (2013.01);
(Continued)

(58) Field of Classification Search
CPC ..... A61B 2503/12; A61B 5/117; A61B 5/369; A61B 5/378; A61B 5/38; A61B 5/381;
(Continued)

(56) References Cited

U.S. PATENT DOCUMENTS 7,594,122 B2  9/2009 Milgramm et al.
8,065,529 B2  11/2011 Hively
(Continued)

FOREIGN PATENT DOCUMENTS

CN    101515200 A    4/2009
CN    106778594 A    12/2016
WO   WO2016113717 A1  7/2016

OTHER PUBLICATIONS

Peter Mell et al, The NIST Definition of Cloud Computing, National Institute of Standards and Technology, Publication 800-145, 2011, entire document.
(Continued)

*Primary Examiner* — Kamran Afshar
*Assistant Examiner* — Brent Johnston Hoover
(74) *Attorney, Agent, or Firm* — Stephanie Carusillo; Andrew D. Wright; Roberts Calderon Safran & Cole, P.C.

(57) ABSTRACT

Aspects provide human detector devices based on neuronal response, wherein the devices are configured to obtain electroencephalogram signals from an entity during a presentation of first sensory information to the entity, and compares the obtained electroencephalogram signals to each of a plurality of trained electroencephalogram signal profile portions that are labeled as the first sensory information that represent electroencephalogram signals most commonly generated by different persons as a function of presentation to the persons of sensory information corresponding to the first sensory information. Thus, the configured processor determines whether the entity is a human as a function of a strength of match of the obtained electroencephalogram signals to ones of the trained electroencephalogram signal profile portions labeled as first sensory information that have highest most-common weightings.

14 Claims, 7 Drawing Sheets

(51) Int. Cl.
  *A61B 5/00*    (2006.01)
  *A61B 5/38*    (2021.01)
  *A61B 5/378*   (2021.01)
  *G16H 10/60*   (2018.01)
  *A61B 5/117*   (2016.01)
  *A61B 5/369*   (2021.01)
  *A61B 5/381*   (2021.01)

(52) U.S. Cl.
  CPC ............... *G06N 3/08* (2013.01); *A61B 5/117* (2013.01); *A61B 5/369* (2021.01); *A61B 5/381* (2021.01); *A61B 5/74* (2013.01); *A61B 2503/12* (2013.01); *G16H 10/60* (2018.01)

(58) Field of Classification Search
  CPC ...... A61B 5/7267; A61B 5/74; G06N 3/0427; G06N 3/08; G16H 10/60; G16H 50/70
  See application file for complete search history.

(56) References Cited

U.S. PATENT DOCUMENTS

| | | | |
|---|---|---|---|
| 8,135,957 | B2 | 3/2012 | Dinges et al. |
| 9,058,473 | B2 | 6/2015 | Navratil et al. |
| 9,672,760 | B1* | 6/2017 | Breuer .................. H04L 9/3247 |
| 2005/0261803 | A1 | 11/2005 | Seth et al. |
| 2008/0229408 | A1 | 9/2008 | Dinges et al. |
| 2008/0294907 | A1 | 11/2008 | Hively |
| 2009/0063866 | A1 | 3/2009 | Navratil et al. |
| 2009/0156956 | A1 | 6/2009 | Milgramm et al. |
| 2012/0136273 | A1 | 5/2012 | Michelson, Jr. |
| 2017/0270411 | A1* | 9/2017 | Kocher .................. A61B 5/291 |
| 2017/0346817 | A1* | 11/2017 | Gordon .............. G06K 9/00885 |
| 2018/0293484 | A1* | 10/2018 | Wang ....................... G06F 3/167 |
| 2019/0228357 | A1* | 7/2019 | Fisher .................... G06N 7/005 |

OTHER PUBLICATIONS

M. Poulos et al, On the use of EEG features towards person identification via neural networks, Medical Informatics and the Internet to Medicine, 2001, pp. 1-2.

Ramaswamy Palaniappan, Two-Stage Biometric Authentication Method Using Thought Activity Brain Waves, International Journal of Neural Systems, World Scientific Publishing Company, 2008, pp. 59-66.

Julie Thorpe et al, Pass-thoughts: Autehnticating with Our Minds, ACM, 2006, pp. 45-56.

Wikipedia, Brain-computer interface, https://en.widipedia.org/wiki/Brain%E2%80%93computer_interface, 2017, pp. 1-14.

Wired Staffwired Staff, Your Thoughts Are Your Password, https://www.wired.com/2006/04/your-thoughts-are-your-password/?currentPage=all, 2006, entire document.

Shahnawaz Khan, Password detection via imagined wrist movement in BCI, IEEE Explore, Conference: Computer Science and Information Technology, 2009, entire document.

David MacDonald et al, Captcha Alternatives and thoughts, WCAG WG, https://www.w3.org/WAIGL/wiki/index.php?title=Captcha_Alternatives_and_thoughts&oldid-5904, 2015, entire document.

Sebastian Anthony, Berkeley researchers replace passwords with passthoughts by reading your mind, Https://WWW.Extremetech.com, Computing (Https://WWW.Extremetech.com/Category/Computing), 2013, entire document.

Neurosky, Bod and Mind. Quantified, Useful, Applicable Brain Activity Algorithms, Get Your MindWave Mobile Headset to Experience Brainwave Powered Apps, 2017, entire document.

Owasp, Authentication Cheat Sheet, https://www.owasp.org/index.php/Authentication_Cheat_Sheet, 2017, pp. 1-8.

\* cited by examiner

NEURAL RESPONSE HUMAN DETECTOR

BACKGROUND

"Bots" are applications running on computer processors in response to the execution of scripts and other programming codes and instructions, and that are designed to emulate human or "humanlike" behavior as online and other input activity to networked resources. Bots are often used to access networked resources through ports and ingress mechanisms that are intended to provide access to real people (humans), to provide services to the humans, or from the inputs provided by humans. Bots gain entry through such mechanisms by spoofing human behavior, fooling the mechanism into accepting their inputs as those of humans.

Bots may be used to create spam, ghost accounts, distributed denial-of-service (DDos) attacks, service disruptions, manipulate ratings, influence elections, otherwise generate fraudulent networked resource inputs and website traffic. For example, a DDoS attack occurs when multiple systems flood the bandwidth or resources of a targeted system, usually one or more web servers. Such an attack is often the result of multiple compromised systems (for example, a "botnet") flooding the targeted system with traffic.

A variety of methods and systems are deployed to distinguish between human inputs and bot access and inputs, in order to secure network and virtualized service environments from bots. For example, CAPTCHA (Completely Automated Public Turing Tests to Tell Computers and Humans Apart) features or tools are commonly used to ensure that user input has not been generated by a computer, generally requiring that the user type-in the letters of a distorted image, sometimes with the addition of an obscured sequence of letters or digits that appears on the screen. CAPTCHAs are generally designed to require the simultaneous use of three separate abilities—invariant recognition, segmentation, and parsing—to correctly complete the task with any consistency. Invariant recognition refers to the ability to recognize the large amount of variation in the shapes of letters. While there are nearly an infinite number of versions for each character that a human brain can successfully identify, the same is not true for a computer, and CAPTCHA systems general try to present differing lettering formations that are difficult for a computerized bot to reliably decode.

Segmentation, or the ability to separate one letter from another, may also be difficult for a bot to perform. Accordingly, CAPTCHA processes often present characters in crowded-together formats, with no white space in between. Bots may also have limited abilities in decoding individual characters based on the context established by surrounding letters, and thereby to correctly parse or identify each character. For example, in one segment of a CAPTCHA, a letter might look like an "m." Only after a whole word including the letter is recognized to establish a context (for example, "fumble") does it become clear to the human reader that the letter must be "u" and not an "m."

Each of these problems poses a challenge for a computer bot in isolation, and CAPTCHA processes often require the execution of all three at the same time to lower the probability that the bot can solve a given CAPTCHA challenge. Unlike computers, humans excel at this type of task. While segmentation and recognition are two separate processes necessary for understanding an image for a computer, they are part of the same process for a person. For example, when an individual understands that the first letter of a CAPTCHA is an "a", that individual also understands where the contours of that "a" are, and where it melds with the contours of the next letter. Additionally, the human brain is capable of dynamic thinking based upon context, able to keep multiple explanations alive and then pick the one that is the best explanation for the whole input based upon contextual clues. This also means it will not be fooled by variations in letter.

However, some automated processes can defeat or work around obstacles presented by CAPTCHA challenges and gain access to resources intended only for direct human access. CAPTCHA tools also impose requirements on user inputs that may not be easily accessible or executable by users, wherein some users may not successfully complete a CAPTCHA test and thereby gain access to networked resources. For example, an image-based CAPTCHA can be very difficult or impossible to complete for users who have comprised vision (for example, are blind, or color-blind, or have macular degeneration or other low-vision abilities). While some CAPTCHA tools offer audio alternatives to users who are visually impaired, the audio alternatives may be difficult to interpret accurately without knowledge of the visual context of the original image, or to remember a series of recited letters accurately, or to understand if the user has low language skills with the language used to convey the audio alternative, or if the human user has other cognitive impairments. Lastly, successfully completing a CAPTCHA may be time-consuming, leading to loss of human participation (and the associated use of the networked resources offered by service providers) through the unwillingness of users to agree to incur inconveniences imposed on the user by the CAPTCHA tool.

SUMMARY

In one aspect of the present invention, a computerized method for a human detector based on neuronal response includes executing steps on a computer processor. Thus, a computer processor is configured to obtain electroencephalogram signals from an entity during a presentation of first sensory information to the entity. The configured processor compares the obtained electroencephalogram signals to each of a plurality of trained electroencephalogram signal profile portions that are labeled as the first sensory information, wherein the electroencephalogram signal profile portions labeled as the first sensory information represent electroencephalogram signals most commonly generated by a plurality of different persons as a function of presentation to the different persons of sensory information corresponding to the first sensory information. Thus, the configured processor determines whether the entity is a human as a function of a strength of match of the obtained electroencephalogram signals to ones of the plurality of trained electroencephalogram signal profile portions labeled as first sensory information that have highest most-common weightings.

In another aspect, a system has a hardware processor in circuit communication with a computer readable memory and a computer-readable storage medium having program instructions stored thereon. The processor executes the program instructions stored on the computer-readable storage medium via the computer readable memory and is thereby configured to obtain electroencephalogram signals from an entity during a presentation of first sensory information to the entity. The configured processor compares the obtained electroencephalogram signals to each of a plurality of trained electroencephalogram signal profile portions that are labeled as the first sensory information, wherein the electroencephalogram signal profile portions labeled as the first sensory information represent electroencephalogram signals most commonly generated by a plurality of different persons as a function of presentation to the different persons of sensory information corresponding to the first sensory information. Thus, the configured processor determines whether the entity is a human as a function of a strength of match of the obtained electroencephalogram signals to ones of the plurality of trained electroencephalogram signal profile portions labeled as first sensory information that have highest most-common weightings.

In another aspect, a computer program product for a human detector based on neuronal response has a computer-readable storage medium with computer readable program code embodied therewith. The computer readable hardware medium is not a transitory signal per se. The computer readable program code includes instructions for execution which cause the processor to obtain electroencephalogram signals from an entity during a presentation of first sensory information to the entity. The processor is caused to compare the obtained electroencephalogram signals to each of a plurality of trained electroencephalogram signal profile portions that are labeled as the first sensory information, wherein the electroencephalogram signal profile portions labeled as the first sensory information represent electroencephalogram signals most commonly generated by a plurality of different persons as a function of presentation to the different persons of sensory information corresponding to the first sensory information. Thus, the processor is caused to determine whether the entity is a human as a function of a strength of match of the obtained electroencephalogram signals to ones of the plurality of trained electroencephalogram signal profile portions labeled as first sensory information that have highest most-common weightings.

BRIEF DESCRIPTION OF THE DRAWINGS

These and other features of embodiments of the present invention will be more readily understood from the following detailed description of the various aspects of the invention taken in conjunction with the accompanying drawings in which.

DETAILED DESCRIPTION

Figure 1:
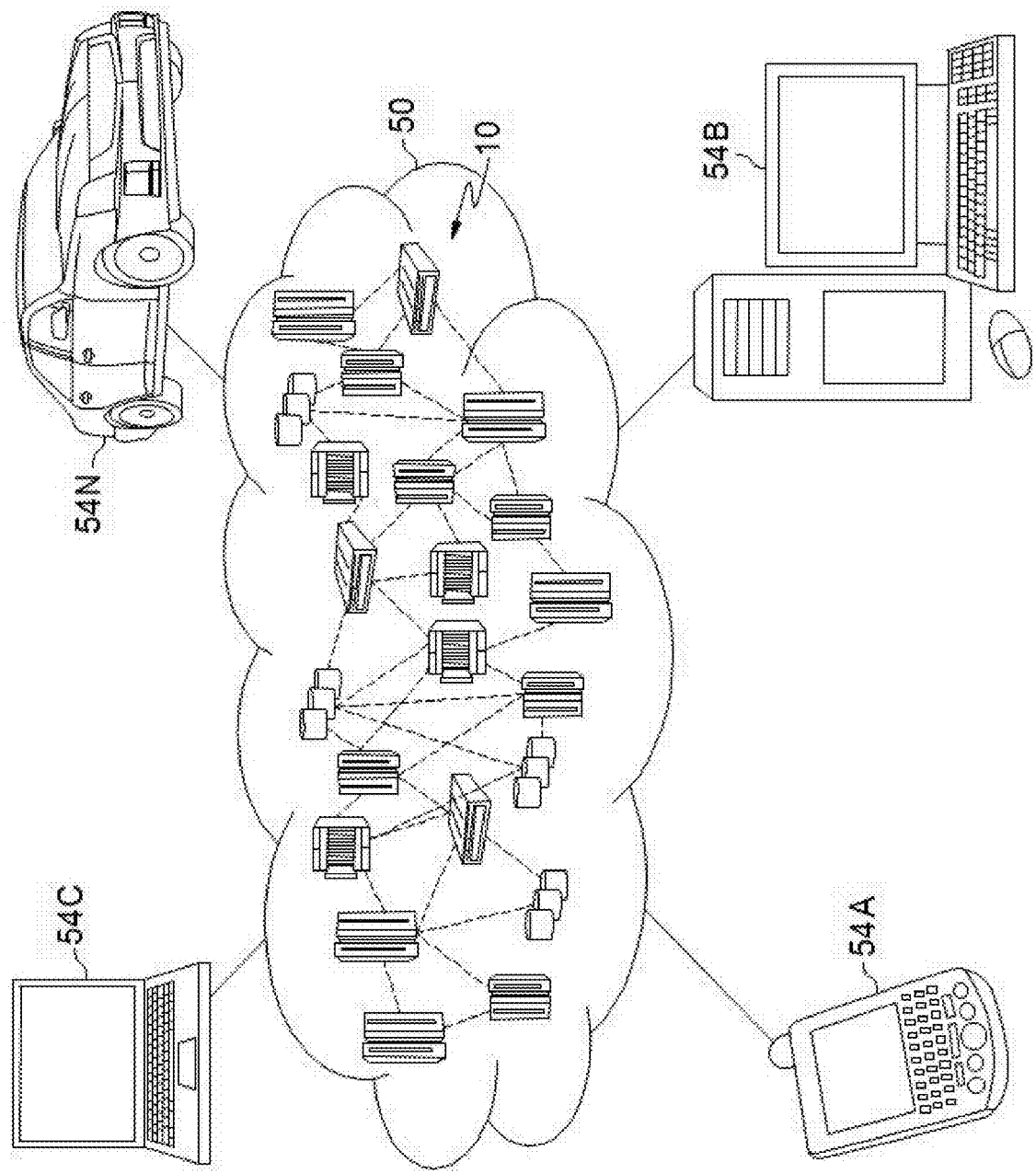
FIG. 1 depicts a cloud computing environment according to an embodiment of the present invention.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and be rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Referring now to FIG. 1, illustrative cloud computing environment 50 is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 1 are intended to be illustrative only and that computing nodes 10 and cloud computing environment 50 can communicate with any type of computerized device over any type of network and/or network addressable connection (e.g., using a web browser).

Figure 2:
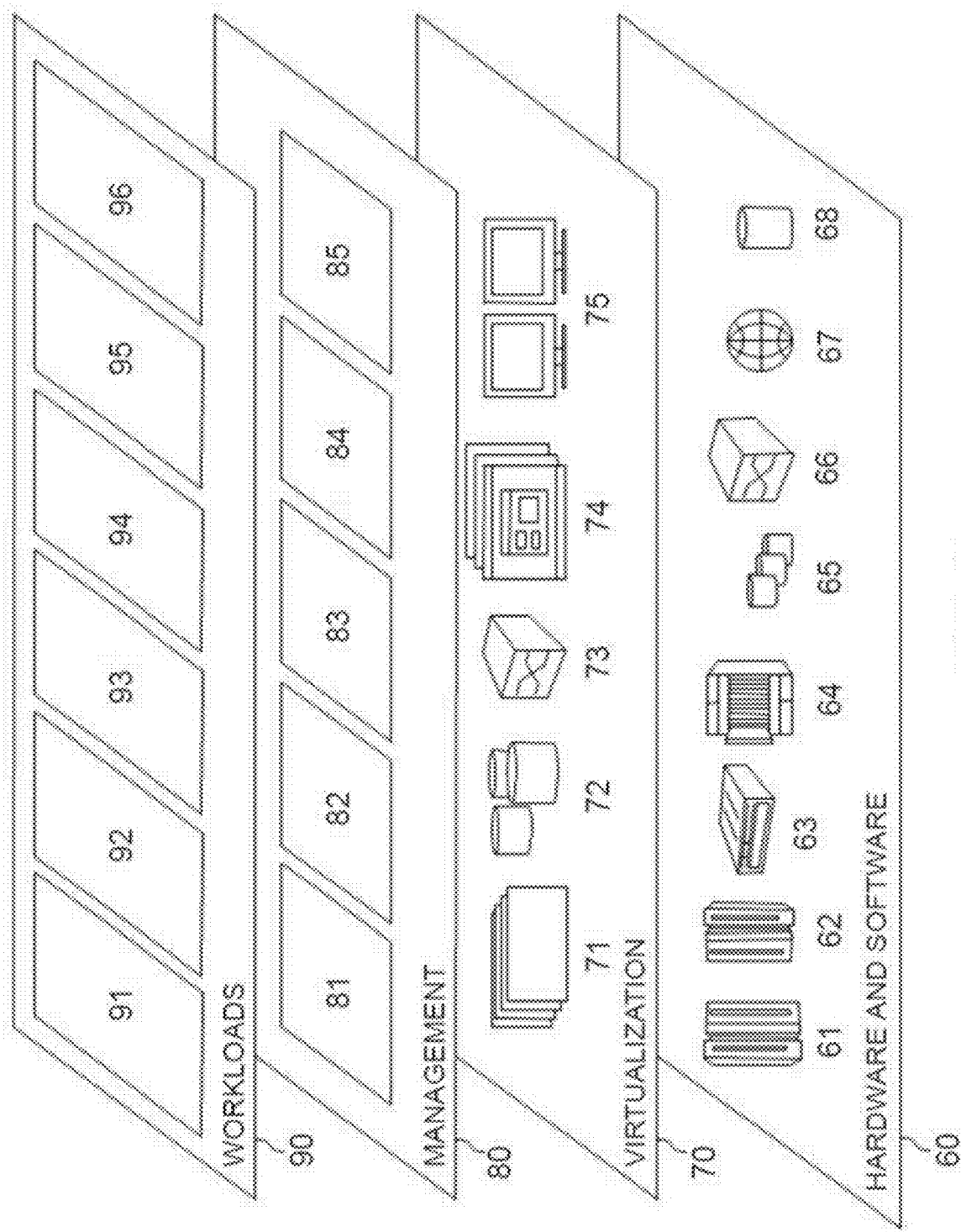
FIG. 2 depicts abstraction model layers according to an embodiment of the present invention.

Referring now to FIG. 2, a set of functional abstraction layers provided by cloud computing environment 50 (FIG. 1) is shown. It should be understood in advance that the components, layers, and functions shown in FIG. 2 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and processing for a human detector based on neuronal response according to aspects of the present invention 96, as discussed more fully below.

Figure 3:
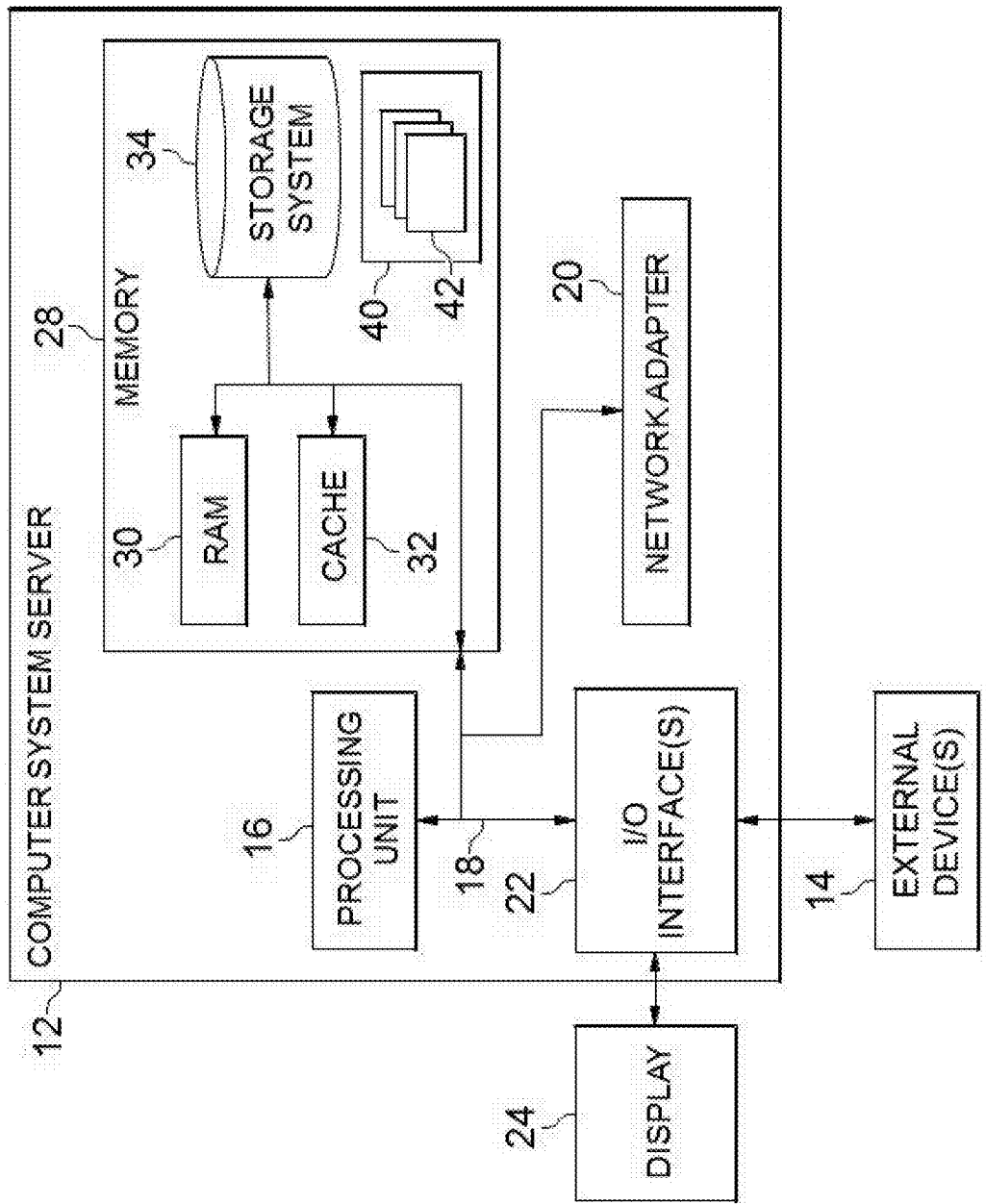
FIG. 3 depicts a computerized aspect according to an embodiment of the present invention.

FIG. 3 is a schematic of an example of a programmable device implementation 10 according to an aspect of the present invention, which may function as a cloud computing node within the cloud computing environment of FIG. 2. Programmable device implementation 10 is only one example of a suitable implementation and is not intended to suggest any limitation as to the scope of use or functionality of embodiments of the invention described herein. Regardless, programmable device implementation 10 is capable of being implemented and/or performing any of the functionality set forth hereinabove.

A computer system/server 12 is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

The computer system/server 12 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

Figure 4:
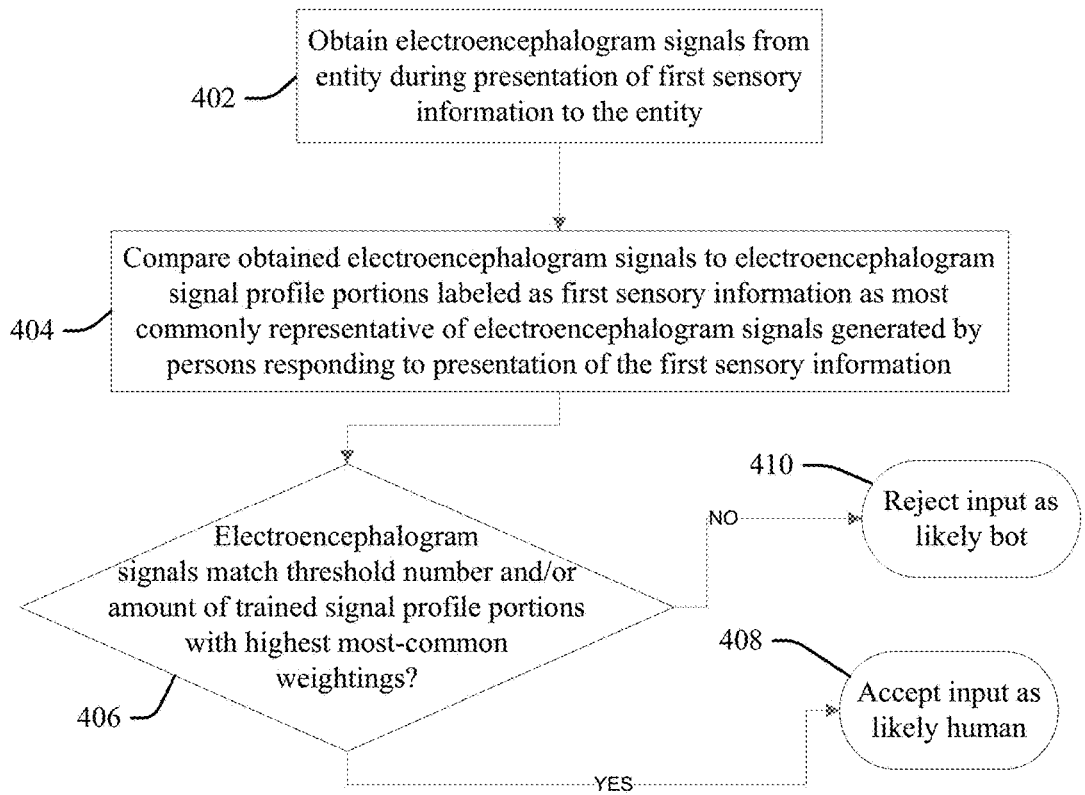
FIG. 4 is a flow chart illustration of an embodiment of the present invention.

FIG. 4 illustrates training a human detector based on neuronal response according to the present invention. Aspects are configured to utilize electroencephalogram (EEG) signals obtained from an entity representing itself as a human, which are generally obtained from a headset device or other device worn or otherwise deployed to capture EEG signals from a person, as will be appreciated by one skilled in the art. Thus, at 402 a processor configured according to an aspect of the present invention (the "configured processor") obtains electroencephalogram (EEG) signals from an entity during a presentation of first sensory information to the entity.

At 404 the configured processor compares the electroencephalogram signals obtained from the entity during the presentation of the first sensory information to each of a plurality of trained electroencephalogram signal profile portions that are labeled as the first sensory information. More particularly, the electroencephalogram signal profile portions labeled as the first sensory information represent electroencephalogram signals that are selected via a training process to be those portions most commonly representative (have highest common weighting values) of EEG signals generated by a plurality of different persons in response to (as a function of) presentation to the different persons of the first sensory information, or of sensory information corresponding thereto.

At 406 the configured processor determines whether the entity is (likely) a human or a bot (a computer application simulating the presence of a human) as a function of a strength of match of the electroencephalogram signals provided by the entity during the presentation of the first sensory information to the entity to highest weighted ones of the plurality of trained electroencephalogram signal profile portions labeled as first sensory information. More particularly, at 406 the configured processor determines whether the obtained entity electroencephalogram signals match a threshold number, or amount, of ones of the plurality of trained electroencephalogram signal profile portions labeled as first sensory information that have the highest most-common weightings. If the threshold comparison is satisfied at 406, then the configured processor determines that the entity supplying the EEG signals at 402 is (likely) a human at 408. Otherwise, if the threshold comparison is not satisfied at 406, then the configured processor determines that the entity is a bot at 410.

Figure 5:
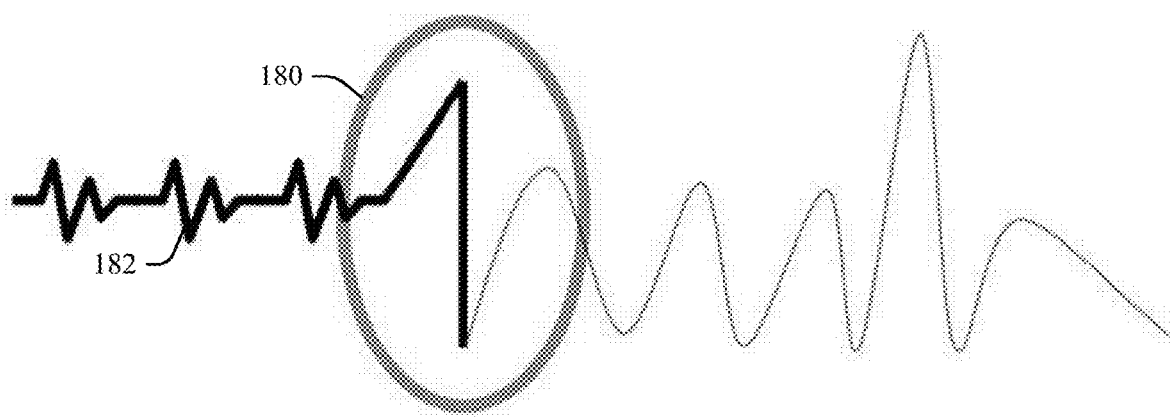
FIG. 5 is a graphic illustration of an electroencephalogram waveform.

FIG. 5 is a graphic illustration of a representation of an EEG signal waveform 182 acquired from a person in response to presentation of sensory information, wherein time defines a horizontal axis for the waveform 182, which shows changing values of amplitude (along a vertical axis normal to the horizontal axis) over time, and wherein the changing values of amplitude over time define a profile attribute of the EEG signal. In response to determining that a profile portion 180 matches a labelled profile portion, aspects may determine an indication or likelihood that the signal is generated by a human, or increase a most-common weighting value of the matching labeled portion in a training process as discussed below.

Figure 6:
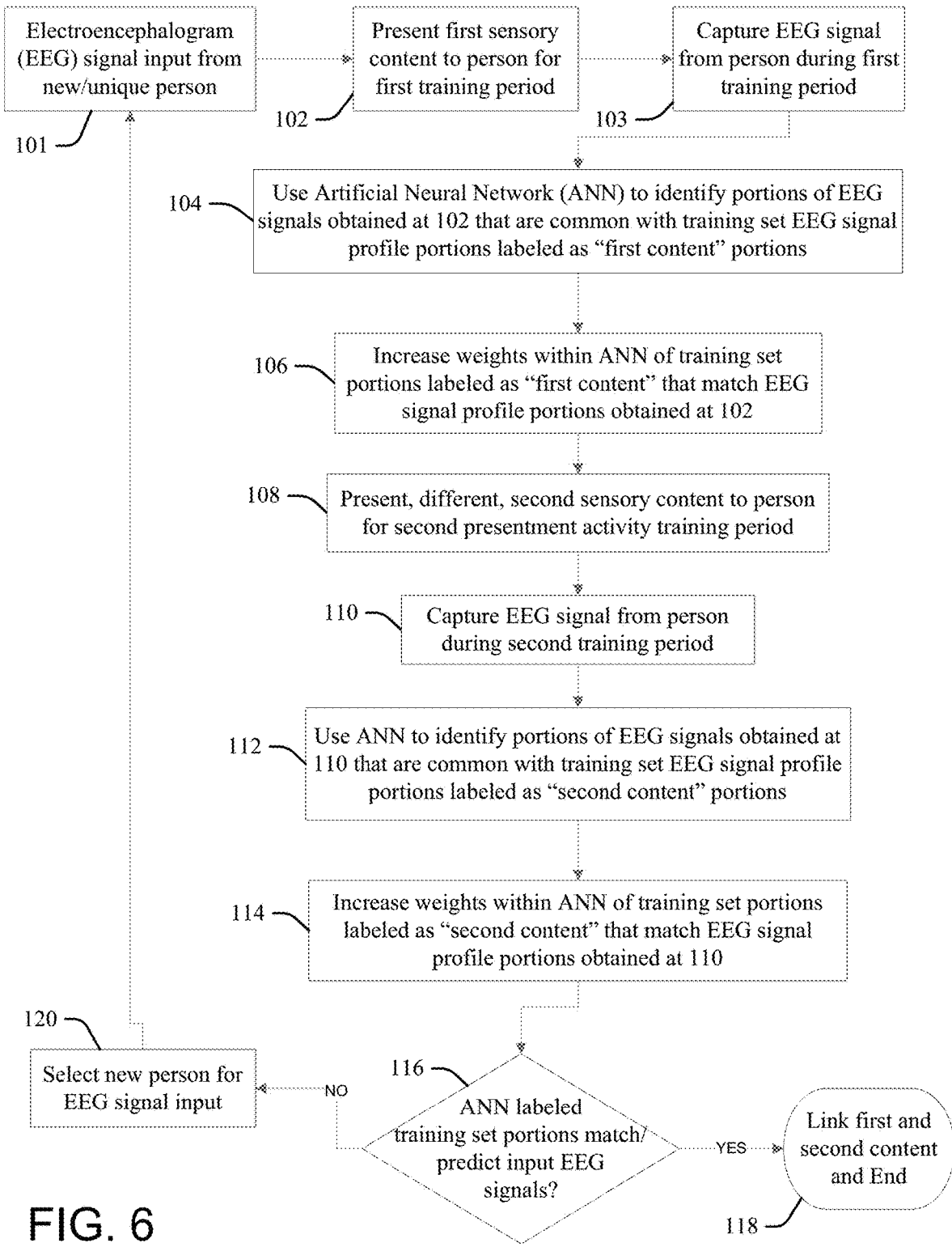
FIG. 6 is a flow chart illustration of an embodiment of the present invention.

FIG. 6 illustrates a training process that identifies, and weights, portions of EEG signals obtained from persons to reflect commonalities with signals obtained from other persons. Thus, in response to identifying an EEG signal input 101 from a person, at 103 a processor configured according to an aspect of the present invention (the "configured processor") obtains EEG signals from the person's input 101 during a first training time period, wherein the electroencephalogram signals are generated by the person in response to presentation of a first amount of sensory information to the person during the first training period at 102.

At 104 the configured processor uses an Artificial Neural Network (ANN) to compare the EEG signals obtained at 103 to trained EEG signal profile portions obtained from other persons during training periods wherein the electroencephalogram signals were generated by each of the other persons in response to presentation of corresponding (first) sensory information to the persons during corresponding (first) training periods, and wherein EEG signal portions that were commonly obtained from the other persons (replicated or similar in amplitude and profile over a portion or time for a plurality of the other persons) are labeled as "first sensory information/data" training set portions.

At 106 the configured processor generates or revises most-common weights or weighting factors within the ANN of the labeled training set portions in response to the comparison at 104: increasing the most-common weights of the training set portions labeled as "first sensory information" that are common with EEG signal profile portions obtained at 103, and/or decreasing the most-common weights of the training set portions labeled as "first sensory information" that are not in common (are dissimilar or not strongly similar to) the EEG signal portions obtained at 103.

An ANN is a computational model based on the structure and functions of biological neural networks, and may be considered nonlinear statistical data modeling tools where the complex relationships between inputs and outputs are modeled or patterns are found. Information that flows through the network affects the structure of the ANN because a neural network changes ("learns") relationship values based on inputs and outputs. The ANN system learns (progressively improves performance) to do tasks by considering examples, generally without task-specific programming. Thus, in the present example, the training set EEG signal profile portions obtained from other persons during corresponding activity training periods are labeled as the "activity" signal portions within a training set that is compared by the configured processor to the signals obtained at 103, to identify those portions at 104 that match the labelled training set portions, and to responsively label these identified portions as the same "activity" signal portions; and to further adjust (increase) the weight of the matching signal portions within the training set more heavily relative to the other signal portions within the training set that do not match EEG signal portion profiles obtained at 103.

With each new set of signals obtained from a different person at 101, the ANN thereby learns and fine tunes the weights of the labeled portions of the training set EEG signal profile portions at 106, increasing weights for those labeled with the corresponding activity that match to the activity signals from the current person, relative to other signal portions labeled as the activity that do not match the profile portions of EEG signals obtained at 103, and wherein the weights are used to select portions for application to EEG signals obtained from others in future iterations.

At 108 the configured processor presents different, second sensory stimulus or data to the person for another (second) presentment activity training period, and at 110 obtains EEG signals from the person's input 101 during this second, presentment activity training period.

At 112 the configured processor uses the ANN to compare the EEG signals obtained at 110 to EEG signal profile portions obtained from other persons during presentment of sensory information corresponding to the second sensory information and labeled as "second sensory information" portions, to thereby identify profile portions of the EEG signals obtained at 110 that are common with the training set portions labeled as second sensory information portions. At 114 the configured processor generates or revises most-common weighting factors within the ANN of the training set portions labeled as second sensory information in response to the comparison: generally increasing the most-common weights of those that are determined to be similar in profile to portions of the EEG signal profile portions obtained at 110, and decreasing the most-common weights of others that are determined to be dissimilar.

At 116 the configured processor determines whether the highest-weighted training set portions labeled "first sensory information" match or generally correspond to (and thereby predict) a threshold number of portions of the EEG signals obtained from the person during the first training period at 103; and whether the highest-weighted training set portions labeled "second sensory information" match or generally correspond to, and thereby predict, a threshold number of portions of the EEG signals obtained from the person during the second training period at 110. The threshold number of portions of the EEG signals is selected to be large enough to represent an EEG signal signature of a person, to be recognizable and distinct from other "signatures" representative of the EEG signals of other people.

If both conditions are met (meeting a logical AND condition), then the training set, and associated ANN, are considered trained and ready for application to EEG signal inputs to verify that the EEG signal inputs are from a human, and not from a bot. Thus, the first and second sensory content presentations are linked together as an associated pair for use in verifying human entities, and the process ends at 118.

Otherwise, if either condition is not met at 116, the configured processor iteratively selects another, different person for providing EEG signals at 120, and returns to 101 to obtain EEG signals from the new person, to repeat the steps at 102 through 114 until both conditions are satisfied at 116.

In some "baseline" embodiments, the first activity period is a "no activity" training period or phase that establishes a null or baseline EEG signal profile for the person providing the EEG signal input, relative to EEG signals generated in response to a presentment activity of the second sensory stimulus or data presented with respect to an identifiable item, sensation, etc., during the second training period that triggers mental activity by the user to identify the item or sensation, etc. Thus, the obtained EEG signals are generated by the person during the first training period wherein the configured processor does not present sensory (image, auditory, taste, smell or physical sensation) stimulus or data to the person to receive and interpret. As the configured processor does not present sensory data, the person is not mentally reacting to or interpreting the sensory data while generating the EEG signals obtained at 103.

In some of said "baseline" aspects, the configured processor conveys instructions to the person at 102 to enter a "no activity" phase of mental activity for the first training period, such as by actively clearing their mind of all images or sounds or thoughts of images or sounds, and to suppress new thoughts, images or sounds from arising, except perhaps for thoughts or images associated with breathing and sitting quietly, etc. Thus, in the present example, each of the other persons used to generate the labelled training data sets were instructed to enter a "no activity" phase of mental activity for corresponding training periods to generate the training set portions, wherein at 104 the configured processor identifies profile portions of the EEG signals obtained at 103 that are common with the labeled training set portions.

In the "baseline" embodiments, the second sensory stimulus or data is a "presentment activity" with respect to an identifiable item, sensation, etc., that triggers mental activity by the user to identify the item/sensation. Thus, the presentment activity training period or phase at 110 obtains EEG signals while the person is asked to process an image (for example, to identify a tree, table, person or other object, or to identify an activity depicted in the image (a person running, smiling, etc.), complete a math problem, identify a missing item on a picture, etc.; to identify auditory data (a spoken word or number, or number of different notes or tones presented via an audio speaker to the person); to describe a sensation (for example, a pulsing pressure on a finger, a heat sensation, etc.); and still other examples will be apparent to one skilled in the art; to thereby acquire EEG signals at 110 while the person is actively engaged in mental activity needed to perform the identification, or counting or memorization and recall, etc. task. Thus, the training set EEG signal profile portions obtained from other persons during corresponding presentment activity training periods are labeled as "presentment activity" signal portions within the training set compared by the configured processor to the signals obtained at 110, to identify those portions at 112 that match the training set portions labeled as presentment activity, and to responsively label these identified portions as "presentment activity" signal portions; and to further adjust (increase) the weight of the matching signal portions labeled as presentment activity within the training set more heavily relative to the other signal portions within the training set labeled as presentment activity that do not match EEG signal portion profiles obtained at 110.

Some embodiments determine and train the labeled "second sensory information" portions as differences (delta) between values of attributes (amplitude, volume, etc.) of the respective EEG signals obtained in association with the respective baseline (first, no-activity) and second (activity) presentments. Humans generally present differences (deltas) between EEG signals generated in baseline no-activity periods, relative to and between performing different activities (listening to speech, generating speech, reading, standing-up, etc.), identifying or responding to different types of stimulus (processing a sudden sound while reading, watching and understanding a multimedia video), etc. These deltas may be captured in training the ANN on the different EEG signals, and used by the aspects to accurately identify if an entity submitting an EEG input user is a real person and not a bot.

Other embodiments may present sensory stimulus or data at each of the first and second training periods that differs with respect to data attributes, to trigger EEG signal generations that are distinct and different from each other as a result in differences of the sensory stimulus or data presented at each of the first and second training period: for example, the entity providing the signals may be asked to count a number of tones played to the entity during the first training period, and asked to identify an image of a red apple during the second training period, and still other examples will be apparent to one skilled in the art.

Embodiments of the invention utilize EEG signal comparison to distinguish human EEG signal inputs from spoofed signals by considering EEG signals generated by a same person in processing different, linked (first and second) sensory data. Thus, different EEG signals having different characteristics are generated by a same person, decreasing the likelihood that a bot will successfully spoof each of the different EEG signals used to train the ANN during the first and second training period, or to spoof a delta or difference between the respective, labelled EEG signal portions.

In addition to baseline-activity associations, linking the first and second sensory presentations may be based on type, wherein other sensory presentations of a similar type may satisfy a linking relationship. For example, where the first sensory presentation is a baseline, "no activity" type, and second sensory presentation is an "image recognition type" (for example, the person is asked to identify an image of an apple), the baseline may be linked to a plurality of sensory presentations of the same "image recognition type" (for example, the person is asked to identify an image of a table with four legs, or of a red automobile, etc.). Thus, a difference or delta in a type or other attribute of the first and second sensory presentations is utilized to generate a corresponding different/delta in qualities of the respective EEG signals generated (energy, amplitude, waveform frequencies), wherein this difference is represented in the weights allocated within the ANN, and thereby useful in distinguishing humans from bots in submitting the respective EEG signals.

Aspects of the present invention provide alternative mechanisms to CAPTCHA and other prior art processes for identifying human users of network connections (and rejecting bots), by leveraging distinguishing profile portions of human brain waves for identification, wherein portions common among large pluralities of persons, yet distinct from one another with respect to differences in sensory information presented to the persons for processing and thereby generating the profile portions, are identified by training an Artificial Neural Network (ANN): with the different EEG signals generated by different persons with respect to similar or common stimuli. During a training procedure, multiple persons are used to train the network on EEG signals generated in response to the presentation of pairs of different, visual, acoustical or other sensory input provided signals. The different signal groupings (for example, pairs of positive (item presentation) and negative (no presentation or activity) presentations) train the ANN, wherein the network is trained with a set of weighting factors that correspond to the specific sensory information presented to the human trainers.

The combination of the trained weighting factors and the Artificial Neural Network (ANN) is used as a signature method or process to identify humans and distinguish them from bots. During training or application, a person visually, acoustically or otherwise receives identifiable signals, and responsively generates EEG signals during the mental activity required by the person to identify the presented sensory information signal. Aspects train the ANN to recognize EEG signals that are common across all users, by weighting these common signal profile portions highest for selection for application to match the EEG signals obtained from others in response to similar sensory stimulus. Captured individual signals are used as input for comparison to the highest-weight, labelled portions of the ANN, to decide as to whether an incoming signal is an EEG signal from a human, rather than a fabricated signal from a bot. Thus, the signals are compared by the trained ANN to a repository of labelled EEG signals. If the outcome of the ANN matches an expected outcome (a set of labeled signal portions common across a plurality of persons used for the training the ANN), aspects of the present invention determine that the associated networked resource access, web activity, etc., is generated by a human and not a bot.

Aspects of the present invention create databases or other repository of EEG results based on (generated from) replicable presentations of specific and sensory stimulus or data. The results are categorized (weighted) via ANN processes by similarity of EEG results across all humans used to generate the data set, wherein similarity is defined by percentages or other metrics of similarity between the results. By using machine learning the aspects recognize and differentially weight profile portion patterns based on the categorized results, which are used to improve the categorizations.

Aspects inherently identify common profile portions within EEG results as a function of a variety of different characteristics and categories of the sensory data presented that result in identifiable EEG signal portions that are common or similar across the persons used to train the ANN. For example, if the stimulation provided to a person is a picture of a red car of a particular make, model or type, the EEG signals may be generated in response to the person thinking about the car (object identification), the color (property), shape (feature), brand (characteristic), etc. Where the EEG signals are trained from a plurality of presentations to different persons that have the same categories (attributes, characteristics, etc.), the EEG result profile portions may be labeled or flagged with each of these categories. This increases the chances of a positive match, because when the aspect system presents the same image to another user, the response provided will be matched not just with the results of other cars, but also with other results having the same color, brand, feature, etc. Differences between EEG signals generated from car images that differ as to color, brand, feature, etc., will be automatically and autonomously be determined by the ANN, as represented in corresponding similarities or differences in the respective weightings of labeled EEG signal portions executed by the ANN, based on similarities or differences in color, shape, object type or category, etc., with respect to presented stimuli.

Aspects may use crowd-sourcing to generate large data sets from large pluralities of persons, which will correspondingly improve the learning of weighting profile portions over the time, thereby increasing the accuracy and effectiveness of the process.

Aspects may also select presented sensory information to match a characteristic of the person or entity being tested to one common to the persons used to train the EEG signal comparison portions, one that is characteristic of the training persons. Illustrative but not limiting or exhaustive examples of considered characteristics include demographic data, client category, job description or skill sets, employer identity, and still others will be apparent to one skilled in the art. Aspects may thus limit training database creation to EEG signals of users of a shared service, such as administered by a service provider to a client base of users, which enables clients to use the aspects for their own systems, and to tailor the stimulus and generated, weighted EEG profiles to meet the needs of their clients. For example, for a software company the sensory stimulus objects and concepts may include software industry prompts that would be recognized and more commonly processed by the users in generating the EEG signals, thereby enhancing the ability to determine common EEG signal outputs for a given stimulus across the client base. Tailoring to a closed set of training users may also improve identification of commonalities in EEG signals, as they may share a common way of thinking about certain sensory stimulus or data items.

Figure 7:
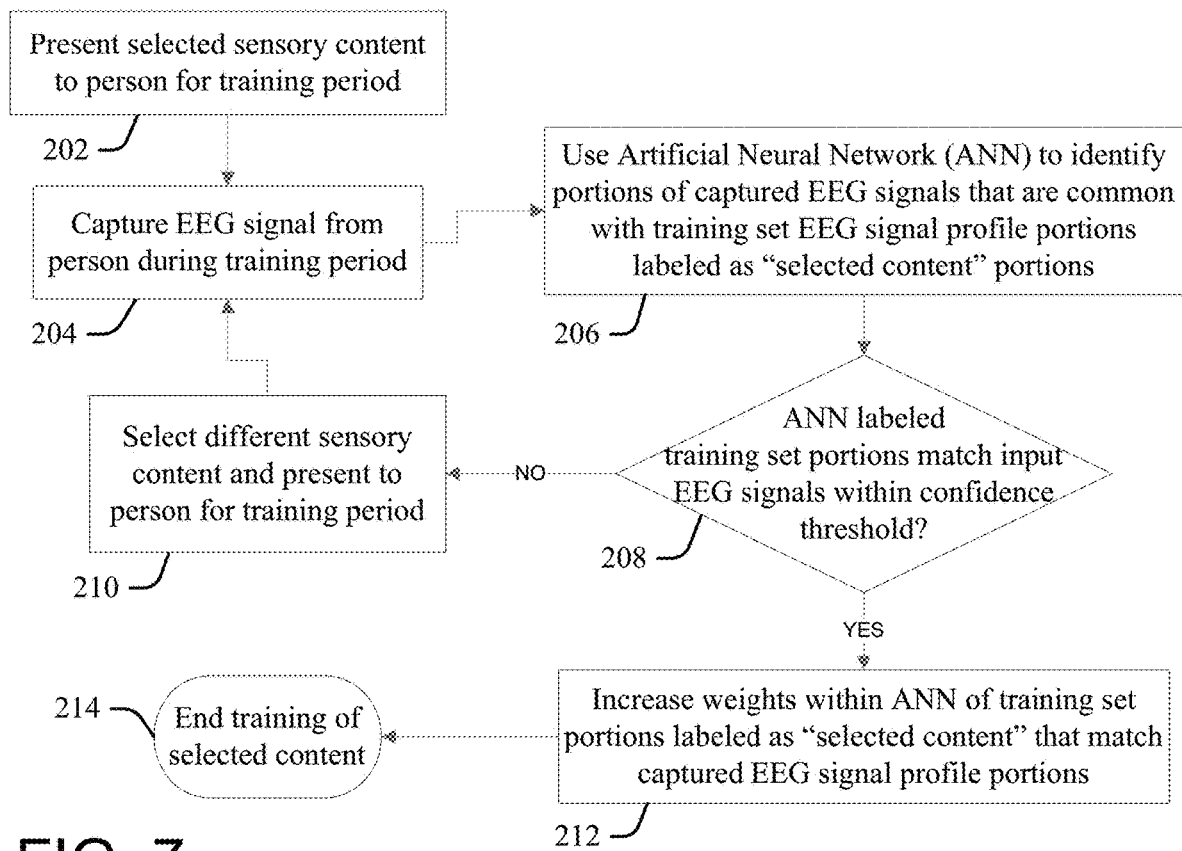
FIG. 7 is a flow chart illustration of an embodiment of the present invention.

FIG. 7 illustrates one embodiment of the present invention wherein the trained data acquired from a person is tested to meet minimum criteria before it is used to train the ANN. More particularly, at 202 a processor configured according to an aspect of the present invention (the "configured processor") presents selected sensory content to a person. At 204 the configured processor captures EEG signals from a person during a training period, and 206 uses an Artificial Neural Network (ANN) to identify portions of captured EEG signals that are common with training set EEG signal profile portions labeled as "selected content" portions.

At 208 the configured processor determines whether the ANN labeled training set portions match input EEG signals within a confidence threshold. If not, then the configured processor iteratively selects different sensory content at 210, presents the different selected content to the person for the training period at 204, and repeats the determinations at 206 and 208 until the threshold condition is met at 208, wherein the configured processor increases weights within ANN of training set portions labeled as "selected content" that match captured EEG signal profile portions at 212, and ends training with respect to the selected content at 214.

Figure 8:
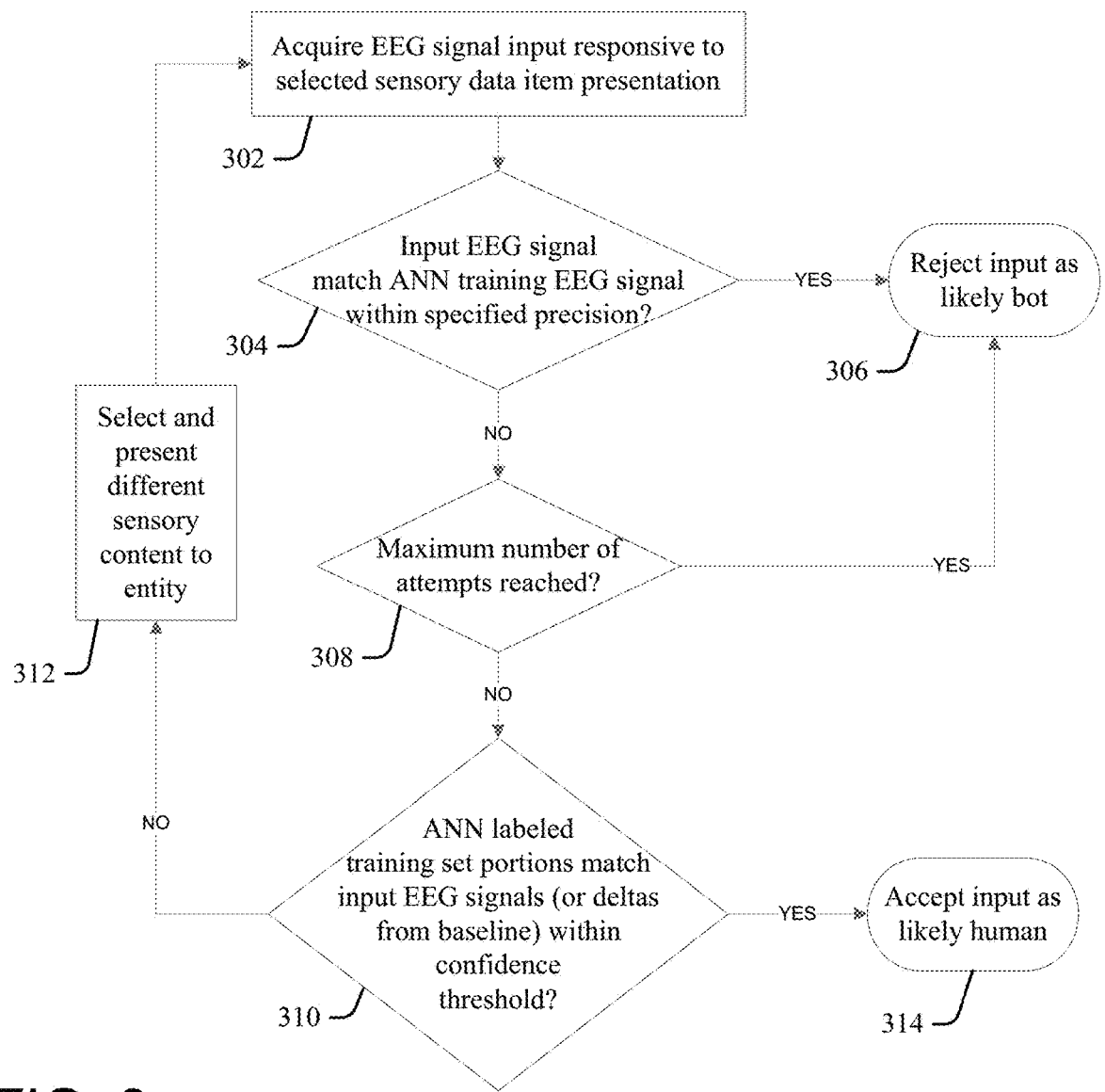
FIG. 8 is a flow chart illustration of an embodiment of the present invention.

Pursuant to the aspect illustrated in FIG. 7, labeled dataset weighting may be personalized for each person providing captured EEG signals, wherein the aspect iteratively selects and presents different stimuli until acceptable EEG signals are captured from the person providing the training data. As different users may respond more strongly or reliably to different sensory stimuli in generating reliable and consistent EEG signal outputs, the present aspects iteratively present different stimuli until the generated and captured EEG signal meets a requisite confident level or threshold at 208 (for example, the amplitudes are consistent over time and meet minimum thresholds, or they match a minimum number of appropriately (matching) labeled profiles that are weighted/trained within the ANN, etc.). The confidence level is generally obtained once the captured EEG signals achieve a level of similarity to the trained labeled portions above a specified threshold, which are selected and dependent on personal attributes or needs of the user FIG. 8 illustrates an embodiment of the present invention that uses the ANN trained by the embodiments of the present invention to verify that an EEG signal received as an input for access to a networked resource is generated by a human and not by a bot. At 302 a processor configured according to an aspect of the present invention (the "configured processor") acquires an EEG signal input responsive to (subsequent to, or associated with) the presentation of a selected sensory data item within a networked resource portal (for example, a log-in web page, an initial greeting screen, etc.).

At 304 the configured processor compares the acquired input signal to the EEG signals used to train the ANN device or mechanism (this, to files saved within a memory, cloud device or service or other repository of the ANN comprising the EEG signals of the persons used to train the ANN). EEG signals captured from different people generally show some degree of variance, due to differences in physiology between different people. To validate the input as more likely human than merely copied and bot-generated, at 304 the configured processor verifies that the input EEG signal is not an exact match to any of the stored EEG signals, thereby failing to show the level of variance expected between EEG signals captured from different people. Thus, in one example where the specified precision value is determined to be 1% (as EEG signals compared within an applicable metric should vary by more than 1%), the configured processor determines at 304 whether the percentage of match, or probability of match, to any of the stored signals is no greater than 99.0%. If the match or probability exceeds this precision factor, then at 306 the configured processor rejects the input signal as likely from a bot, as it was likely copied from an existing EEG signal and used to spoof the presence of a human.

Thus, if determined at 304 that the input signal is not an exact match to any of the stored EEG signals (is different by at least the specified precision value), at 308 the configured processor verifies that the present input signal session has not exceeded a permissible number of log-in or other verification attempts. If determined at 308 that the session has exceeded a permissible number of log-in/verification attempts, then at 306 the configured processor rejects the input signal as likely from a bot; otherwise (if determined at 308 that the session has not exceeded a permissible number of log-in/verification attempts) then at 310 the configured processor determines whether the ANN training set portions labeled with the selected sensory data item presented at 302 match portions of the input EEG signals, or deltas between the portions of the input EEG signals and baseline signals determined for the entity (as discussed above), within a confidence threshold.

If the configured processor determines at 310 that the labeled ANN training set portions or associated deltas do not match portions of the input EEG signals within the confidence threshold, at 312 the configured processor iteratively selects and presents another, different sensory data item to the entity attempting to log in at 314, wherein the processes returns to 302. This aspect recognizes that a failure to match to any of the label signal portions within the ANN at 310 may be due to physiological attributes of a person entity, or noise within the system, and thus the aspect gives the entity another chance to qualify, by processing different sensory items, including those that meet linking requirements, until they pass at 310, or too many attempts are made at 308.

Thus, if the configured processor determines at 310 that the labeled ANN training set portions or associated deltas do match portions of the input EEG signals within the confidence threshold, then at 314 the configured processor determines that the input is verified as likely from a human, rather than a bot.

Signal verification at 304 may also include determinations as to an origin of the captured signal, wherein the configured processor verifies that the input EEG signal comes directly from an EEG device (for example, by running a script on an end-user machine, or through executing a handshake routine, etc.). This will avoid bots or hackers from spoofing a human signal input at 302 via using hard-coded samples of EEG signals. Additional inputs from a device or user may be used to validate that EEG reads come from a user (and is not instead a file copy or recording created at a previous time). Examples of verification inputs include unique device and sensor identifications from personal user mobile devices, such as smart watches, smartphones, heartbeat sensors, accelerometers, etc. Pre-registered Internet-of-Things (IoT) devices, such as smart house sensors, may also be used to verify that the user is at home, including to crosscheck IoT data with internet protocol (IP) addresses of data received to confirm the user location.

Aspects of the present invention may also incorporate additional verification routines and processes: for example, the configured processor may challenge an entity providing an EEG signal to perform an action (talk, move, blink, etc.), wherein the EEG signal will be representative of the physical action performed. Such embodiments may enable more efficient identification, and require less training, where the EEG signals resulting from performing the requested actions are more strongly unique and replicable relative to mental processing routines, having characteristics that are easier for the system to identify as uniquely-associated EEG signals.

Aspects may track known bots, and generate a blacklist of bots that have tried to simulate an EEG response, via by recording data and metadata associated with known spoofing attempts (username, email address, IP address, server locations, etc.). Verification at 304 may further require a determination that data indicative of an origin of the EEG signal acquired at 302 is not on the black list.

Aspects of the present invention train databases of EEG results based on a given stimulation, which may be categorized by similarity of the EEG result, and which similarity may be defined by percentages of similarity between the results. Aspects use machine learning to create patterns based on the categorized results which will be used to improve the categorization. Each EEG result can be on several categories, for example if the stimulation provided to the user is in the form of a picture of a red car, the user's brain may think of (process an image of) a car (object), the color (property), the shape (feature), the brand (characteristic), etc., and some aspects may flag EEG results with respect to each of these different categories, increasing the chances of a positive match when the system presents the same image to another user (as the response provided will be matched not just with the results of other cars, but also with other reads with the same color, brand, feature, etc.). Trained and labeled EEG signal portion sets may be shared (for example, as a service) to allow other users to deploy within their own systems.

Aspects may also personalize the trained and labeled EEG signal portion sets personalized for each user. For example, aspects may upload a plurality of associated EEG reads for a given user, requesting several EEG reads until the system reaches a confidence level for that user, which may vary based on user characteristics and needs.

Aspects may create multi factor (or multilayer) inputs from an EEG signal (response). Rather than merely associating an EEG signal to a stimulus of a human thought in one dimension, aspects add additional layers of abstraction by considering the delta between activities, and the different characteristics between different actions performed by a human.

The terminology used herein is for describing aspects only and is not intended to be limiting of the invention. As used herein, the singular forms "a", "an" and "the" are intended to include the plural forms as well, unless the context clearly indicates otherwise. It will be further understood that the terms "include" and "including" when used in this specification specify the presence of stated features, integers, steps, operations, elements, and/or components, but do not preclude the presence or addition of one or more other features, integers, steps, operations, elements, components, and/or groups thereof. Certain examples and elements described in the present specification, including in the claims, and as illustrated in the figures, may be distinguished, or otherwise identified from others by unique adjectives (e.g. a "first" element distinguished from another "second" or "third" of a plurality of elements, a "primary" distinguished from a "secondary" one or "another" item, etc.) Such identifying adjectives are generally used to reduce confusion or uncertainty, and are not to be construed to limit the claims to any specific illustrated element or embodiment, or to imply any precedence, ordering or ranking of any claim elements, limitations, or process steps.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A computer-implemented method for a human detector based on neuronal response, the method comprising executing on a computer processor:

obtaining first training electroencephalogram signals from a first person during a first training period, wherein the first training electroencephalogram signals are generated by the first person in response to presentation of first sensory information to the first person during the first training period;

comparing the obtained first training electroencephalogram signals to each of a plurality of trained electroencephalogram signal profile portions that are labeled as the first sensory information;

weighting each of the plurality of trained electroencephalogram signal profile portions that are labeled as the first sensory information training set portions to increase weight values in response to determining a similarity to profile portions of the obtained first training electroencephalogram signals, and to decrease the weight values in response to determining a dissimilarity to the profile portions of the obtained first training electroencephalogram signals;

training the plurality of trained electroencephalogram signal profile portions labeled as the first sensory information by iteratively repeating, for each of a plurality of new persons, until determining that a threshold number of ones of the training set portions labeled first sensory information that have highest most common weights have a threshold weighting value:

obtaining new person training electroencephalogram signals generated by each new person in response to presentation of the first sensory information to each new person during first training periods;

comparing the obtained new person training electroencephalogram signals to each of the plurality of trained electroencephalogram signal profile portions labeled as the first sensory information training set portions; and revising the weighting of each of the plurality of trained electroencephalogram signal profile portions that are labeled as the first sensory information training set portions to increase weight values in response to determining a similarity to profile portions of the obtained new person training electroencephalogram signals, and to decrease the weight values in response to determining a dissimilarity to the profile portions of the obtained new person training electroencephalogram signals;

obtaining first electroencephalogram signals from an entity during a presentation of the first sensory information to the entity;

comparing the obtained first electroencephalogram signals to each of the plurality of trained electroencephalogram signal profile portions that are labeled as the first sensory information, wherein the electroencephalogram signal profile portions labeled as the first sensory information represent electroencephalogram signals generated by a plurality of different persons as a function of the presentation to the different persons of sensory information corresponding to the first sensory information;

determining whether the entity is a human as a function of a strength of a match of the obtained first electroencephalogram signals to at least one of the plurality of trained electroencephalogram signal profile portions labeled as first sensory information that are above a threshold weight; and determining that the entity is not human in response to determining that the obtained first electroencephalogram signals match one of the trained electroencephalogram signal profile portions labeled as first sensory information within a specified precision value.

2. The method of claim 1, further comprising:

obtaining second electroencephalogram signals from the entity in response to presentation of second sensory information to the entity that is different from the first sensory information;

comparing the obtained second electroencephalogram signals to each of a plurality of trained electroencephalogram signal profile portions that are labeled as the second sensory information, wherein the second sensory information training set portions labeled as the first sensory information represent electroencephalogram signals generated by the plurality of different persons as a function of presentation to the different persons of sensory information corresponding to the second sensory information; and wherein the determining whether the entity is a human is further determined as a second function of a strength of a match of the obtained second electroencephalogram signals to at least one of the plurality of trained electroencephalogram signal profile portions labeled as the second sensory information that is above a threshold weight.

3. The method of claim 1, further comprising:

selecting the first sensory information to match a characteristic of the entity that is common to a characteristic of the plurality of different persons, wherein the characteristic of the entity is selected from the group consisting of demographic data, client category, job description, a skill set and employer identity.

4. The method of claim 1, further comprising:

verifying that an input of the obtained first entity electroencephalogram signals comes directly from an approved device as a function of a process selected from the group consisting of running a script on an end-user machine providing the input of the entity electroencephalogram signals, and executing a handshake routine on the end-user machine; and determining that the entity is not human in response to determining a failure of the verifying.

5. The method of claim 1, further comprising:

obtaining baseline entity electroencephalogram signals from the entity during a presentation of baseline sensory information to the entity that is different from the first sensory information;

determining a delta value as a difference between a value of an attribute of the obtained first electroencephalogram signals and a value of the attribute of the obtained baseline electroencephalogram signals;

wherein the comparing the obtained first electroencephalogram signals to each of the plurality of trained electroencephalogram signal profile portions that are labeled as the first sensory information comprises comparing the determined delta value to each of a plurality of delta electroencephalogram signal profile portions labeled as the first sensory information, wherein the plurality of delta electroencephalogram signal profile portions labeled as the first sensory information are each determined as differences between electroencephalogram signals obtained from ones of the plurality of different persons during presentation of the first sensory information, relative to baseline entity electroencephalogram signals obtained from the at least one of the plurality of different persons during presentation of the baseline sensory information.

6. The method of claim 5, wherein the presentation of the baseline sensory information is a "no activity" presentation phase.

7. The method of claim 1, further comprising:
integrating computer-readable program code into a computer system comprising a processor, a computer readable memory in circuit communication with the processor, and a computer readable storage medium in circuit communication with the processor; and
wherein the processor executes program code instructions stored on the computer-readable storage medium via the computer readable memory and thereby performs the obtaining the electroencephalogram signals from the entity during the presentation of the first sensory information to the entity, the comparing the obtained electroencephalogram signals to each of the plurality of trained electroencephalogram signal profile portions that are labeled as the first sensory information, and the determining whether the entity is the human as the function of the strength of the match of the obtained electroencephalogram signals to the at least one of the plurality of trained electroencephalogram signal profile portions labeled as first sensory information that are above the threshold weight.

8. The method of claim 7, wherein the computer-readable program code is provided as a service in a cloud environment.

9. A system, comprising:
a processor;
a computer readable memory in circuit communication with the processor; and
a computer readable storage medium in circuit communication with the processor;
wherein the processor executes program instructions stored on the computer-readable storage medium via the computer readable memory and thereby:
obtains first training electroencephalogram signals from a first person during a first training period, wherein the first training electroencephalogram signals are generated by the first person in response to presentation of first sensory information to the first person during the first training period;
compares the obtained first training electroencephalogram signals to each of a plurality of trained electroencephalogram signal profile portions that are labeled as the first sensory information;
weights each of the plurality of trained electroencephalogram signal profile portions that are labeled as the first sensory information training set portions to increase weight values in response to determining a similarity to profile portions of the obtained first training electroencephalogram signals, and to decrease the weight values in response to determining a dissimilarity to the profile portions of the obtained first training electroencephalogram signals;
trains the plurality of trained electroencephalogram signal profile portions labeled as the first sensory information by iteratively repeating, for each of a plurality of new persons, until determining that a threshold number of ones of the training set portions labeled first sensory information that have highest most common weights have a threshold weighting value:
obtains new person training electroencephalogram signals generated by each new person in response to presentation of the first sensory information to each new person during first training periods;
compares the obtained new person training electroencephalogram signals to each of the plurality of trained electroencephalogram signal profile portions labeled as the first sensory information training set portions; and
revises the weighting of each of the plurality of the trained electroencephalogram signal profile portions that are labeled as the first sensory information training set portions to increase weight values in response to determining a similarity to profile portions of the obtained new person training electroencephalogram signals, and to decrease the weight values in response to determining a dissimilarity to the profile portions of the obtained new person training electroencephalogram signals;
obtains electroencephalogram signals from an entity during a presentation of first sensory information to the entity;
compares the obtained first electroencephalogram signals to each of a plurality of trained electroencephalogram signal profile portions that are labeled as the first sensory information, wherein the electroencephalogram signal profile portions labeled as the first sensory information represent electroencephalogram signals generated by a plurality of different persons as a function of the presentation to the different persons of sensory information corresponding to the first sensory information;
determines whether the entity is a human as a function of a strength of a match of the obtained first electroencephalogram signals to at least one of the plurality of trained electroencephalogram signal profile portions labeled as first sensory information that are above a threshold weight; and
determines that the entity is not human in response to determining that the obtained first electroencephalogram signals match one of the trained electroencephalogram signal profile portions labeled as first sensory information within a specified precision value.

10. The system of claim 9, wherein the processor executes the program instructions stored on the computer-readable storage medium via the computer readable memory and thereby:
obtains second electroencephalogram signals from the entity in response to presentation of second sensory information to the entity that is different from the first sensory information;
compares the obtained second electroencephalogram signals to each of a plurality of trained electroencephalogram signal profile portions that are labeled as the second sensory information, wherein the second sensory information training set portions labeled as the first sensory information represent electroencephalogram signals generated by the plurality of different persons as a function of presentation to the different persons of sensory information corresponding to the second sensory information; and determines whether the entity is a human is further determined as a second function of a strength of a match of the obtained second electroencephalogram signals to at least one of the plurality of trained electroencephalogram signal profile portions labeled as the second sensory information that is above a threshold weight.

11. The system of claim 9, wherein the processor executes the program instructions stored on the computer-readable storage medium via the computer readable memory and thereby:

obtains baseline entity electroencephalogram signals from the entity during a presentation of baseline sensory information to the entity that is different from the first sensory information;

determines a delta value as a difference between a value of an attribute of the obtained first electroencephalogram signals and a value of the attribute of the obtained baseline electroencephalogram signals; and compares the obtained first electroencephalogram signals to each of the plurality of trained electroencephalogram signal profile portions that are labeled as the first sensory information by comparing the determined delta value to each of a plurality of delta electroencephalogram signal profile portions labeled as the first sensory information, wherein the plurality of delta electroencephalogram signal profile portions labeled as the first sensory information are each determined as differences between electroencephalogram signals obtained from ones of the plurality of different persons during presentation of the first sensory information, relative to baseline entity electroencephalogram signals obtained from the at least one of the plurality of different persons during presentation of the baseline sensory information.

12. A computer program product for a human detector based on neuronal response, the computer program product comprising:

a computer readable storage medium having computer readable program code embodied therewith, wherein the computer readable storage medium is not a transitory signal per se, the computer readable program code comprising instructions for execution by a processor that cause the processor to:

obtain first training electroencephalogram signals from a first person during a first training period, wherein the first training electroencephalogram signals are generated by the first person in response to presentation of first sensory information to the first person during the first training period;

compare the obtained first training electroencephalogram signals to each of a plurality of trained electroencephalogram signal profile portions that are labeled as the first sensory information;

weight each of the plurality of trained electroencephalogram signal profile portions that are labeled as the first sensory information training set portions to increase weight values in response to determining a similarity to profile portions of the obtained first training electroencephalogram signals, and to decrease the weight values in response to determining a dissimilarity to the profile portions of the obtained first training electroencephalogram signals;

train the plurality of trained electroencephalogram signal profile portions labeled as the first sensory information by iteratively repeating, for each of a plurality of new persons, until determining that a threshold number of ones of the training set portions labeled first sensory information that have highest most common weights have a threshold weighting value:

obtain new person training electroencephalogram signals generated by each new person in response to presentation of the first sensory information to each new person during first training periods;

compare the obtained new person training electroencephalogram signals to each of the plurality of trained electroencephalogram signal profile portions labeled as the first sensory information training set portions; and revise the weighting of each of the plurality of the trained electroencephalogram signal profile portions that are labeled as the first sensory information training set portions to increase weight values in response to determining a similarity to profile portions of the obtained new person training electroencephalogram signals, and to decrease the weight values in response to determining a dissimilarity to the profile portions of the obtained new person training electroencephalogram signals;

obtain electroencephalogram signals from an entity during a presentation of first sensory information to the entity;

compare the obtained first electroencephalogram signals to each of a plurality of trained electroencephalogram signal profile portions that are labeled as the first sensory information, wherein the electroencephalogram signal profile portions labeled as the first sensory information represent electroencephalogram signals generated by a plurality of different persons as a function of the presentation to the different persons of sensory information corresponding to the first sensory information;

determine whether the entity is a human as a function of a strength of a match of the obtained first electroencephalogram signals to at least one of the plurality of trained electroencephalogram signal profile portions labeled as first sensory information that are above a threshold weight; and determine that the entity is not human in response to determining that the obtained first electroencephalogram signals match one of the trained electroencephalogram signal profile portions labeled as first sensory information within a specified precision value.

13. The computer program product of claim 12, wherein the computer readable program code instructions for execution by the processor further cause the processor to:

obtain second electroencephalogram signals from the entity in response to presentation of second sensory information to the entity that is different from the first sensory information;

compare the obtained second electroencephalogram signals to each of a plurality of trained electroencephalogram signal profile portions that are labeled as the second sensory information, wherein the second sensory information training set portions labeled as the first sensory information represent electroencephalogram signals generated by the plurality of different persons as a function of presentation to the different persons of sensory information corresponding to the second sensory information; and determine whether the entity is a human is further determined as a second function of a strength of a match of the obtained second electroencephalogram signals to at least one of the plurality of trained electroencephalogram signal profile portions labeled as the second sensory information that is above a threshold weight.

14. The computer program product of claim 12, wherein the computer readable program code instructions for execution by the processor further cause the processor to:
   obtain baseline entity electroencephalogram signals from the entity during a presentation of baseline sensory information to the entity that is different from the first sensory information;
   determine a delta value as a difference between a value of an attribute of the obtained first electroencephalogram signals and a value of the attribute of the obtained baseline electroencephalogram signals; and
   compare the obtained first electroencephalogram signals to each of the plurality of trained electroencephalogram signal profile portions that are labeled as the first sensory information by comparing the determined delta value to each of a plurality of delta electroencephalogram signal profile portions labeled as the first sensory information, wherein the plurality of delta electroencephalogram signal profile portions labeled as the first sensory information are each determined as differences between electroencephalogram signals obtained from ones of the plurality of different persons during presentation of the first sensory information, relative to baseline entity electroencephalogram signals obtained from the at least one of the plurality of different persons during presentation of the baseline sensory information.

\* \* \* \* \*